(12) United States Patent
Iwahashi et al.

(10) Patent No.: US 8,118,183 B2
(45) Date of Patent: Feb. 21, 2012

(54) DELAMINATABLE LAMINATED BOTTLE

(75) Inventors: Kazuya Iwahashi, Suita (JP); Hirokazu Mihashi, Kameoka (JP); Keiji Hamamoto, Osaka (JP); Masaru Otsuka, Sagamihara (JP); Yorishisa Uetake, Nagoya (JP); Kenji Matsuura, Ibaraki (JP)

(73) Assignees: Taisei Kako Co., Ltd. (JP); Nihon Tenganyaku Kankyusho Co., Ltd. (JP)

( * ) Notice: Subject to any disclaimer, the term of this patent is extended or adjusted under 35 U.S.C. 154(b) by 1355 days.

(21) Appl. No.: 10/541,132

(22) PCT Filed: Feb. 13, 2004

(86) PCT No.: PCT/JP2004/001603
§ 371 (c)(1),
(2), (4) Date: Jun. 29, 2005

(87) PCT Pub. No.: WO2004/071887
PCT Pub. Date: Aug. 26, 2004

(65) Prior Publication Data
US 2006/0054635 A1      Mar. 16, 2006

(30) Foreign Application Priority Data

Feb. 14, 2003 (JP) .................................. 2003-036113

(51) Int. Cl.
*B65D 1/02* (2006.01)
*B65D 77/00* (2006.01)
(52) U.S. Cl. .......... 215/12.2; 215/385; 220/676; 222/95
(58) Field of Classification Search ................ 215/12.2, 215/385, 383; 222/94, 95; 220/676
See application file for complete search history.

(56) References Cited

U.S. PATENT DOCUMENTS

| 2,743,038 | A | * | 4/1956 | Ferries ............................ 222/95 |
| 2,777,612 | A | * | 1/1957 | Bensen ......................... 222/209 |
| 3,662,048 | A | * | 5/1972 | Turner ............................ 264/85 |
| 4,020,978 | A | * | 5/1977 | Szczepanski ................. 222/209 |
| D262,356 | S | * | 12/1981 | Kretz .............................. D9/542 |
| 4,387,816 | A | * | 6/1983 | Weckman ...................... 215/381 |
| 5,002,718 | A | * | 3/1991 | Tanaka et al. ................. 264/530 |
| 5,156,300 | A | * | 10/1992 | Spahni et al. ................. 222/105 |
| 5,344,045 | A | * | 9/1994 | Richter et al. .................... 222/1 |

(Continued)

FOREIGN PATENT DOCUMENTS

JP    2001-105477 A    4/2001

(Continued)

*Primary Examiner* — Sue Weaver
(74) *Attorney, Agent, or Firm* — Wood, Phillips, Katz, Clark & Mortimer

(57) ABSTRACT

A particularly small eyedropper or the like is provided, which has a construction such that, when a body thereof is squeezed, an introduction hole thereof can be easily closed to compress air in a space between an inner layer and an outer layer thereof even in the absence of a check valve in the introduction hole, and defectiveness of the introduction hole can be easily checked. To this end, a test hole (19) communicating with an introduction hole (17) via a space between an outer layer bottle. (1) and an inner layer bag (16) is provided in an outer layer mouth portion (4). The test hole (19) is closed by the inner layer bag (16) and an inside plug (21) fitted in the mouth portion (4). Further, the introduction hole (17) is provided in a middle portion of a body which is pressed by a finger when the bottle is squeezed. The introduction hole (17) is closed by the finger.

4 Claims, 10 Drawing Sheets

U.S. PATENT DOCUMENTS

| | | | |
|---|---|---|---|
| 5,373,967 A * | 12/1994 | Grooms et al. | 222/95 |
| 5,567,377 A * | 10/1996 | Nishigami et al. | 264/515 |
| 6,266,943 B1 * | 7/2001 | Nomoto et al. | 53/410 |
| 6,467,653 B1 | 10/2002 | Hamamoto et al. | |
| 6,581,803 B1 | 6/2003 | Yoshimoto et al. | |
| 6,649,121 B1 | 11/2003 | Hamamoto et al. | |
| 6,672,479 B2 | 1/2004 | Shiraishi et al. | |
| 6,997,337 B1 * | 2/2006 | Wurster | 215/382 |
| 2002/0130139 A1 * | 9/2002 | Shiraishi et al. | 222/105 |

FOREIGN PATENT DOCUMENTS

| | | |
|---|---|---|
| JP | 2001-105478 A | 4/2001 |
| JP | 2001-114328 | 4/2001 |
| JP | 2001-146260 A | 5/2001 |
| JP | 2002-263166 A | 9/2002 |

* cited by examiner

DELAMINATABLE LAMINATED BOTTLE

TECHNICAL FIELD

The present invention relates to a delaminatable laminated bottle which includes an outer layer and an inner layer provided on an inner surface of the outer layer and delaminatable from the outer layer, and a production method for the delaminatable laminated bottle.

BACKGROUND ART

The inventors of the present invention have proposed delaminatable laminated bottles of the aforesaid type as disclosed in the following patent publications 1 to 6.
Patent Publication 1: JP2001-146260-A
Patent Publication 2: JP2001-114328-A
Patent Publication 3: JP2001-105477-A
Patent Publication 4: JP2001-105478-A
Patent Publication 5: JP2001-146260-A
Patent Publication 6: JP2002-263166-A These prior art delaminatable laminated bottles do not require post-processing such as melt-processing or piercing for forming an air introduction hole in an outer later after injection molding of a preform, because the formation of the air introduction hole is achieved with the use of a pin provided in a mold. This is advantageous in that the molding process is simplified and the production is achieved by utilizing an existing production plant which is modified simply by providing the pin in the mold, thereby reducing plant costs. Without the need for the post-processing, there is no possibility of contamination of products with foreign matters due to the post-processing, so that these delaminatable laminated bottles are advantageously utilized particularly as cosmetic containers and medical containers such as eyedroppers. In the prior art delaminatable laminated bottles, a check valve for preventing back flow of air in the air introduction hole is defined by an inner layer mouth portion, thereby achieving simplification of the construction and reduction of the costs.

In order to ensure the functions of the delaminatable laminated bottle and prevent distribution of defective products, it is supposedly important to check for assured formation of the air introduction hole. However, there is no established check method. Particularly for the molding of a small bottle having a volume of about 10 ml, high levels of accuracies are required in various aspects. Therefore, it is primarily important to establish a defective check method.

Where the prior art is applied to a small eyedropper having a volume of about 10 ml and the inner layer of the eyedropper has a thickness sufficient for proper functioning, the ratio of the inner layer thickness to a mouth diameter is increased. Hence, there is a possibility that the inner layer does not properly function as the check valve. Further, where the introduction hole is formed in a bottle body, the introduction hole is liable to be closed when the bottle body is drawn in a blow molding process. Therefore, it is desirable to establish the check method.

DISCLOSURE OF THE INVENTION

It is therefore an object of the present invention to provide a delaminatable laminated bottle which has a construction such that, particularly when it is embodied as a small eyedropper, an introduction hole thereof can be easily closed to compress air between an inner layer and an outer layer thereof by squeezing a bottle body even in the absence of a check valve in the introduction hole and defectiveness of the introduction hole can be easily checked, and to provide a production method for the bottle.

To attain the aforementioned object, the present invention has the following technical features.

A delaminatable laminated bottle according to the present invention comprises: an outer layer bottle having a squeeze-deformable bottomed tubular body, a shoulder portion and a mouth portion connected to an upper edge of the body via the shoulder portion; an inner layer bag provided on an inner surface of the outer layer bottle and delaminatable from the outer layer bottle; the outer layer bottle having an introduction hole for introducing outside air into a space between the outer layer bottle and the inner layer bag; the mouth portion having a test hole communicating with the introduction hole via the space between the outer layer bottle and the inner layer bag; and a member fitted in the mouth portion and having an outlet passage for dispensing contents of the inner layer bag, the member pressing the inner layer bag against the test hole so that the test hole is closed by the inner layer bag and the member.

According to the present invention, whether or not the introduction hole is assuredly formed is determined by checking for air flow from the introduction hole when air is injected into the space between the outer layer bottle and the inner layer bag from the test hole. Since the test hole is closed by the member (e.g., an inside plug or the like) and the inner layer bag, there is no possibility of the leakage of the air which may otherwise occur when the test hole is open during use.

In the inventive delaminatable laminated bottle, the body of the outer layer bottle has a flat tubular peripheral wall which includes a pair of front and rear wall portions spaced a predetermined distance in opposed relation and left and right wall portions respectively connecting left and right edges of the front wall portion to left and right edges of the rear wall portion, and has an anteroposterior thickness which is smaller than a lateral width thereof. The left and right wall portions may each have an arcuate shape with an anteroposteriorly middle portion thereof bulged laterally outward. The body may further have an upper connection portion which connects upper edges of the front and rear wall portions to the shoulder portion, and a lower connection portion which connects lower edges of the front and rear wall portions to a bottom portion thereof. The introduction hole may be provided in a center portion of at least one of the front wall portion and the rear wall portion. The introduction hole may be adapted to be closed by a finger when the body is squeezed to be deformed by pressing the front and rear wall portions by the finger. With this arrangement, when the body of the outer layer bottle is squeezed to be deformed by holding the front and rear wall portions of the bottle on opposite sides of a minor axis thereof, for example, by a thumb and a forefinger, the introduction hole is inevitably closed by the finger to pressurize the air in the space between the inner layer and the outer layer. Therefore, the inner layer bag is shrunk by the pressurized air to dispense the content liquid.

More preferably, the front and rear wall portions may be rigid wall portions which each have a relatively great thickness, and the left and right wall portions may be flexible connection wall portions which each have a relatively small thickness. Further, the upper connection portion and the lower connection portion may be a flexible connection portions which each have a relatively small thickness. Thus, the right and left edges of the front rigid wall portion are respectively connected to the right and left edges of the rear rigid wall portion via the flexible connection wall portions, and upper and lower edges of the rigid wall portions are connected to the shoulder portion and the bottom portion via the flexible connection portions. When the front and rear rigid wall portions are pressed toward each other by two fingers, the entire body is squeezed to be deformed. Even if the bottle has a smaller volume, the bottle can be squeezed to be deformed so that the volume thereof is reduced to the half or smaller. Further, even if the bottle is thus squeezed to be considerably deformed, the bottle is less liable to be broken because the left and right flexible connection wall portions and the upper and lower flexible connection portions are elastically deformed. Therefore, a greater amount of content liquid can be dispensed at a time by squeezing the bottle. Further, the content liquid can be dispensed to the last drop from the delaminatable laminated bottle having the inner layer bag provided in the bottle.

The delaminatable laminated bottle having the aforesaid construction can be produced by a conventionally known blow molding method. The delaminatable laminated bottle is configured so that the rigid wall portions each have a relatively great thickness and the right and left connection wall portions and the upper and lower connection portions each have a relatively small thickness. By varying a blow ratio for the respective portions or varying a wall thickness of a bottle preform for the respective portions, the rigid wall portions are imparted with rigidity so as not to be warped by a pressing force applied by the fingers, and the connection wall portions and the connection portions are imparted with flexibility so as to be elastically deformed to follow parallel displacement of the front and rear rigid wall portions. Outer surfaces of the rigid wall portions are preferably planar, but may be entirely slightly curved outward or inward.

To produce the bottle having the aforesaid construction by the blow molding, the configuration of a shape imparting surface of a mold for the blow molding is preferably modified. In the case of a conventional so-called oval bottle blow-molding mold, for example, a shape imparting surface of the mold is configured so that shape imparting surface portions of the mold on opposite sides of a minor axis of a body of the mold are planar or convexly or concavely curved as having a greater curvature radius than the wall portions on the opposite sides of the minor axis of the bottle body. The wall portions on the opposite sides of the minor axis of the bottle body are formed at a lower blow ratio, and defined as the rigid wall portions each having a greater thickness, and wall portions on opposite sides of a major axis of the bottle body are formed at a higher blow ratio, and defined as the flexible connection wall portions each having a smaller thickness. Further, the shape imparting surface of the blow-molding mold is configured so that projections bulged anteroposteriorly outward are provided on upper and lower sides of the rigid wall portions. Portions of the bottle body on the upper and lower sides of the rigid wall portions are formed at a partly greater blow ratio, and defined as the flexible connection portions each having a smaller thickness.

Where the bottle is a blow-molded plastic bottle, it is preferred that the flexible upper connection portion and the flexible lower connection portion are located anteroposteriorly outward of the rigid wall portions, and the average thickness of these connection portions is smaller than the average thickness of the rigid wall portions. Further, it is preferred that the lateral width of the body is greater than the anteroposterior thickness of the body, and the average thickness of the left and right flexible connection wall portions is smaller than the average thickness of the rigid wall portions. Thus, the bottle can be easily produced at lower costs simply by modifying the configuration of the shape imparting surface of the blow-molding mold as described above without the need for alteration of the construction of the blow molding apparatus and the blow process.

The bottle may be configured so that the body thereof has a laterally elongated oval cross section and the rigid wall portions each have a vertically elongated rectangular shape as seen from the front side. The outer surfaces of the rigid wall portions each have a vertical length of 20 mm or greater, preferably 25 mm or greater. In general, when the bottle body is held and pressed by the fingertips of the two fingers (the thumb and the forefinger), outer surface portions of the bottle body to which a pressure is applied by the fingertips in contact with the outer surface portions each have a vertical length of 1 cm or smaller. In the case of the conventional squeezable bottle, only the portions of the bottle each having a length of about 1 cm in contact with the fingertips are warped to be deformed when the bottle is squeezed by the two fingertips. Therefore, only a very small amount of content liquid is dispensed. In the case of the inventive bottle, on the other hand, the rigid wall portions each having a vertical length of 20 mm or greater are displaced inward of the bottle due to their rigidity to significantly reduce the volume of the bottle when the vertically middle portions of the front and rear rigid wall portions are pressed by the two fingertips. Further, where the outer surfaces of the rigid wall portions each have a lateral width which is greater than one half the lateral width of the entire body (a distance between vertexes of the outer surfaces of the left and right arcuate connection wall portions) and greater than 10 mm, the rigid wall portions can be easily squeezed and, hence, the squeezability of the entire bottle body can be further improved. Where the distance between the outer surfaces of the front and rear rigid wall portions is smaller than the lateral widths of the outer surfaces of the rigid wall portions, the left and right connection wall portions can be smoothly elastically deformed by increasing the curvature radii of the left and right connection wall portions.

More preferably, the left and right connection wall portions and the upper and lower connection portions are adapted to be deformed within elastically deformable ranges so that, when the vertically middle portions of the front and rear rigid wall portions are pressed to be displaced toward each other to positions spaced a distance which is one half an original distance between the middle portions, the upper and lower edges of the rigid wall portions are displaced to follow the displacement of the middle portions of the front and rear rigid wall portions. Further, the left and right connection wall portions and the upper and lower connection portions may be adapted to be deformed within the elastically deformable ranges even if the front and rear rigid wall portions are squeezed to abut against each other.

The inventive delaminatable laminated bottle may further comprise a mouth plug provided in the mouth portion thereof. The mouth plug has an outlet passage through which fluid contained in the inner layer bag is discharged to the outside. The mouth plug may include a dispense valve provided in the outlet passage for opening and closing the outlet passage. The dispense valve may include a valve flange and a valve head, which are preferably connected to each other via a valve sleeve having a flexible structure. The valve flange seals an inner periphery of the outlet passage. The valve head is connected to an inner periphery of the valve flange directly or indirectly via the valve sleeve or the like, and has an orifice which is opened to permit the fluid to flow when a predetermined dispense pressure is applied to the inside of the bag and is closed to prevent the flow of the fluid when the predetermined dispense pressure is removed. Further, the mouth plug may have a support portion which supports the valve head in abutment with the valve head to prevent the orifice of the valve head from being opened when a negative pressure occurs inside the bag. The inside pressure of the bottle should be increased to not lower than the predetermined dispense pressure to open the dispense valve. Since the bottle having the aforesaid construction can be squeezed to be significantly elastically deformed by pressing the entire body of the bottle, it is possible to apply the dispense pressure to the bottle without breakage.

In the inventive delaminatable laminated bottle, a check valve is absent in the introduction hole. Further, the peripheral wall of the body of the outer layer bottle may have a recess indented inward of the bottle or a protuberance projecting outward of the bottle, and the introduction hole may be provided in the recess or the protuberance. The recess or the protuberance is dimensioned so as to be covered with a finger pad and, for example, has a round shape having a diameter of about 5 mm. Thus, a portion of the bottle body to be pressed by the finger is clearly defined, so that even a blind person or a handicapped person can easily use the bottle. Further, the recess or the protuberance can be accurately positioned and shaped by the blow-molding mold. Where the introduction hole is formed in the preform before the blow molding, the position and configuration of the introduction hole of the bottle are liable to be varied after the blow molding. With the provision of the introduction hole in the recess or the protuberance, however, the positional and configurational variations are less conspicuous, thereby improving the appearance of the product.

According to the present invention, a production method for a delaminatable laminated bottle which includes an outer layer and an inner layer provided on an inner surface of the outer layer and delaminatable from the outer layer, the outer layer having an introduction hole for introducing air into a space between the outer layer and the inner layer comprises the steps of: injection-molding an outer layer preform; injection-molding an inner layer preform inside the outer layer preform; blow-molding the delaminatable laminated bottle from a laminate parison including the outer layer preform and the inner layer preform; and performing a defective checking operation.

In the outer layer preform injection molding step, the introduction hole may be formed in the outer layer preform, and a test hole may be formed in a mouth portion of the outer layer preform. In the inner layer preform injection molding step, the inner layer preform may be injection-molded with pins being inserted in the introduction hole and the test hole from an outer periphery of the outer layer preform and with distal ends of the pins being flush with an inner surface of the outer layer preform. In the blow molding step, the parison may be blow-molded with the introduction hole being positioned in a predetermined circumferential position with respect to a blow-molding mold. In the defective checking step, air communication between the test hole and the introduction hole of the delaminatable laminated bottle produced by the blow molding is checked for detecting defectiveness of the introduction hole. Thus, even if a portion of the parison (e.g., a body of the parison) formed with the introduction hole is drawn in the blow molding step, it is possible to check if the introduction hole is closed by the drawing.

In the inventive production method, the air communication check is performed by introducing air from the test hole.

The introduction hole of the outer layer preform has a diameter which is not greater than twice, more preferably not greater than 1.5 times a thickness of a portion of the inner layer preform adjacent to the introduction hole. This prevents the introduction hole from being buried in the inner layer by a blow pressure in the blow molding.

Further, the outer layer may comprise an outer layer bottle having a squeeze-deformable bottomed tubular body, a shoulder portion and a mouth portion connected to an upper edge of the body via the shoulder portion, and the inner layer may comprise an inner layer bag provided on an inner surface of the outer layer bottle and delaminatable from the outer layer bottle. The introduction hole may be provided in a peripheral wall of the body of the outer layer bottle. The blow-molding mold has a shape imparting surface which includes a shape imparting surface portion for forming a recess or a protuberance in a predetermined portion of the peripheral wall of the outer layer bottle including the introduction hole. With this arrangement, the recess or the protuberance is formed in a portion of the bottle body to be pressed by a finger for clearly marking the press portion, so that even a blind person or a handicapped person can easily use the bottle. With the provision of the introduction hole in the recess or the protuberance, positional and configurational variations of the introduction hole are less conspicuous, thereby improving the appearance of the product.

In the inventive production method, it is possible to employ a method and an apparatus for forming a hole only in an outer layer which are disclosed in JP-2001-105477-A.

BRIEF DESCRIPTION OF THE DRAWINGS

FIG. 9(a) is a sectional view of a axially middle portion of the parison (taken along a line D-D in FIG. 9(b)), and FIG. 9(b) is a vertical sectional view of the parison taken along a line C-C;

BEST MODE FOR CARRYING OUT THE INVENTION

Figure 1:
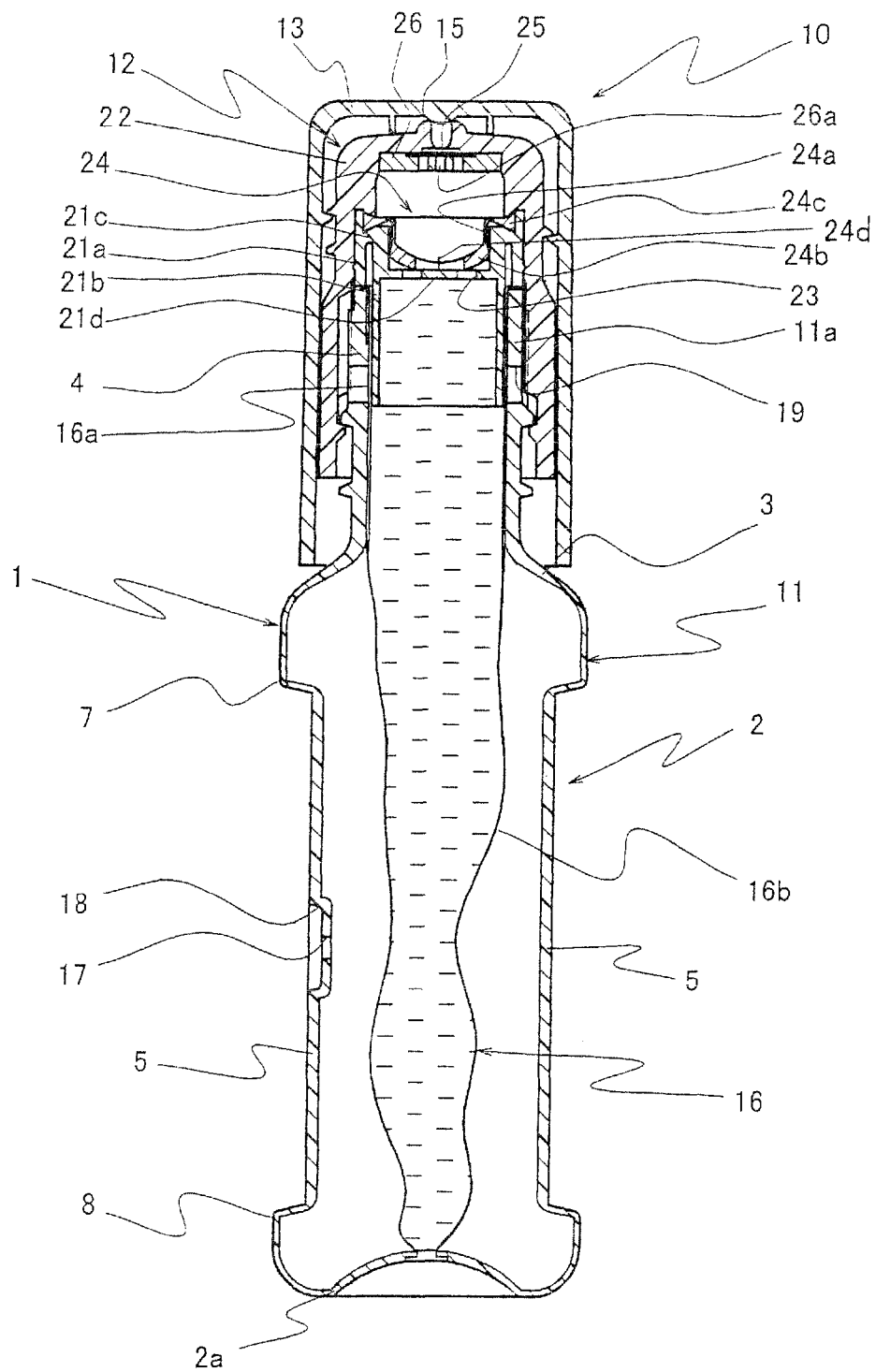
FIG. 1 is a vertical sectional view of an eyedropper including a delaminatable laminated bottle according to one embodiment of the present invention.
Figure 2:
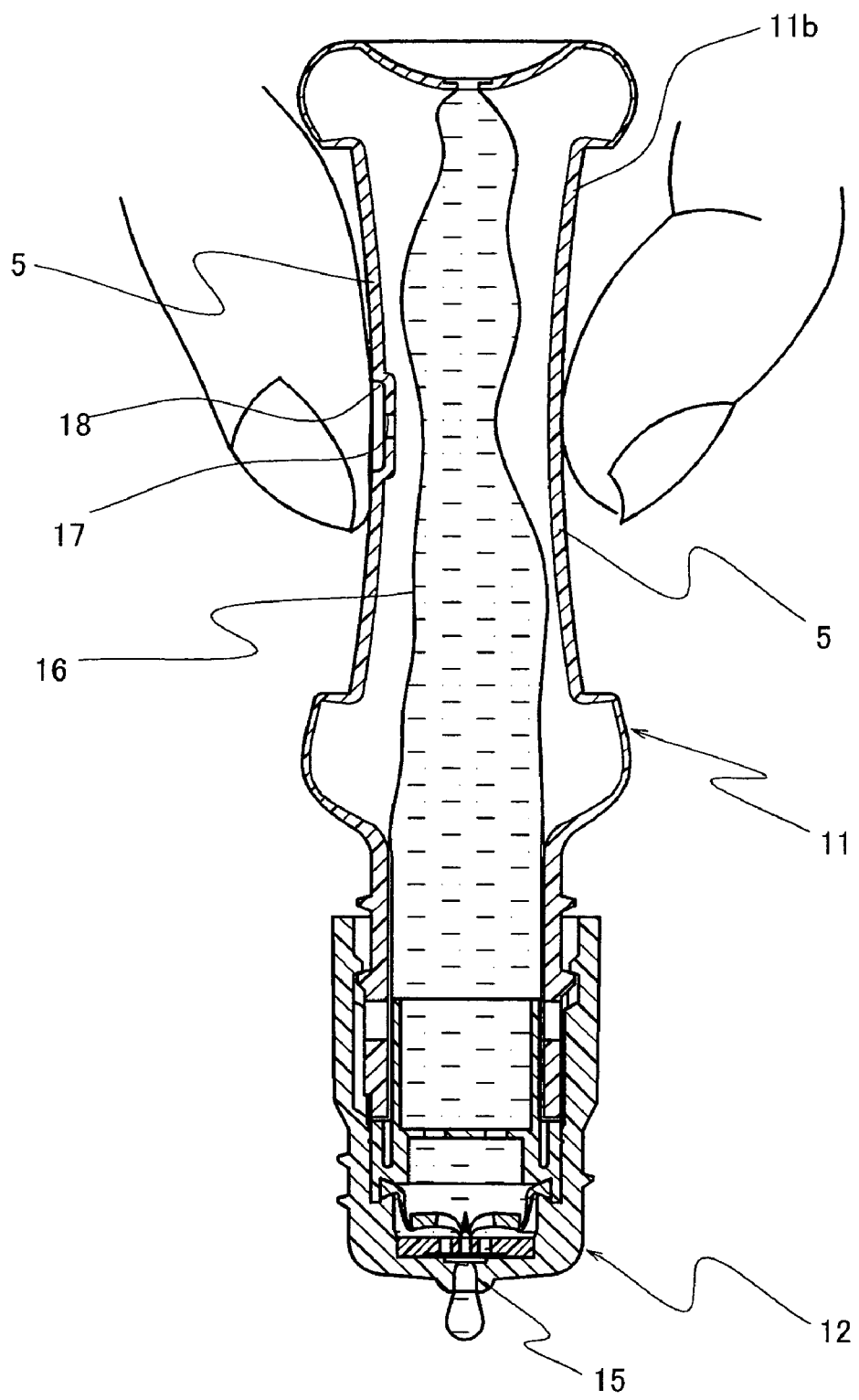
FIG. 2 is a vertical sectional view illustrating how to use the eyedropper.
Figure 3:
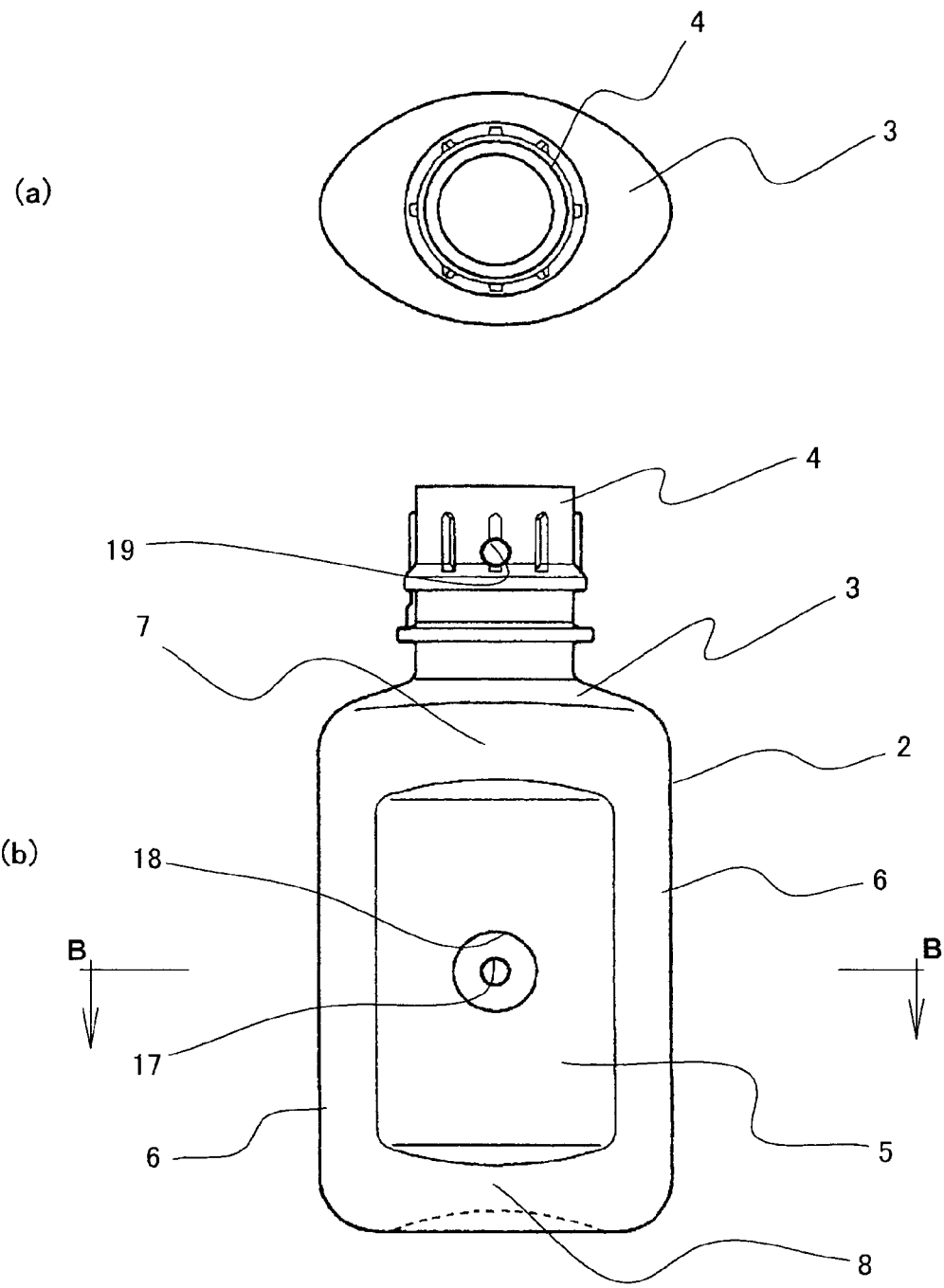
FIGS. 3(a) and 3(b) are a plan view and a front view, respectively, illustrating the overall delaminatable laminated bottle of the eyedropper.
Figure 4:
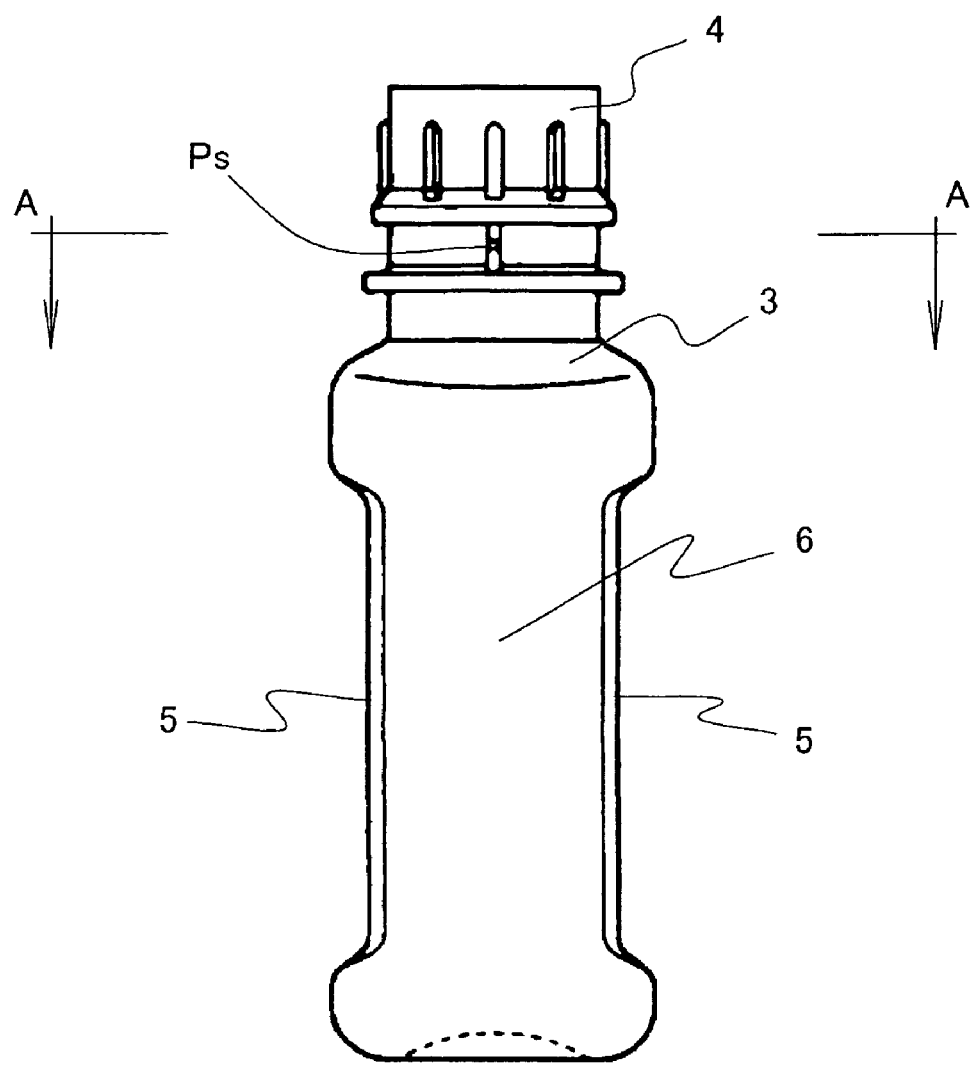
FIG. 4 is a side view of the delaminatable laminated bottle.
Figure 5:
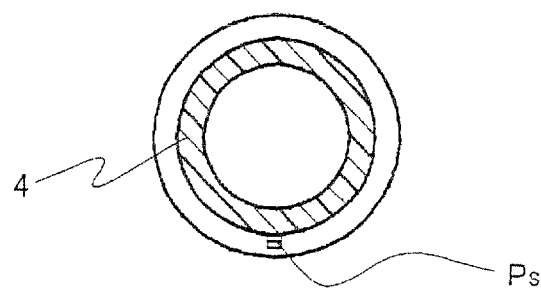
FIG. 5 is a sectional view taken along a line A-A in FIG. 4.

FIGS. 1 and 2 illustrate an eyedropper 10 as a dispenser including a delaminatable laminated bottle according to one embodiment of the present invention. The eyedropper 10 includes a delaminatable laminated bottle 11 of a double layer structure blow-molded from a bottomed tubular laminate parison, a mouth plug 12 attached to a mouth portion 11a of the bottle 11, and a protection cap 13. When a user removes the cap 13 and holds the laminated bottle 11 upside down to press and squeeze a body 11b of the laminated bottle 11, an eye lotion (fluid) in the bottle 11 flows through an outlet passage in the mouth plug 12 thereby to be dropped from a distal nozzle portion 15. Although the bottle 11 is illustrated on an enlarged scale in the figures, the bottle 11 actually has a total height of about 56 mm, and the body 11b has a lateral width of about 25 mm and an anteroposterior thickness of about 17.5 mm. The bottle 11 has a volume of about 10.4 ml.

The laminated bottle 11 has a laminate structure which includes an outer layer bottle 1 (squeeze bottle) defined as an outer layer and an inner layer bag 16 (fluid containing bag) defined as an inner layer. The outer layer bottle 1 and the inner layer bag 16 each have a cylindrical mouth portion and a body having a flat cross section immediately after the blow molding. The outer layer bottle 1 is composed of a synthetic resin such as PET or EVOH, and the inner layer bag 16 is composed of a synthetic resin (e.g., a polyolefin such as polyethylene) which is easily delaminatable from the outer layer bottle 1. The mouth portion of the bag 16 defines an opening for discharging liquid.

Figure 6:
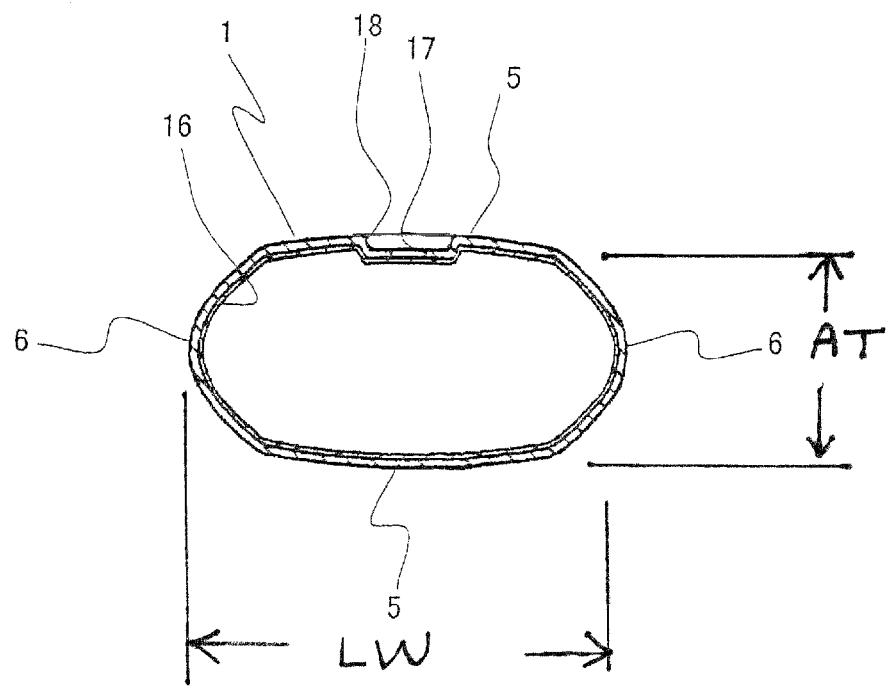
FIG. 6 is a sectional view taken along a line B-B in FIG. 3 [FIG. 3(b)]

As also shown in FIGS. 3 to 6, the outer layer bottle 1 is such that a cylindrical mouth portion 4 is connected to an upper end of an elastically squeeze-deformable bottomed tubular body 2 via a shoulder portion 3 having a diameter gradually decreasing toward its upper end. As shown in FIG. 6, the body 2 has a flat oval peripheral wall which includes front and rear rigid wall portions 5 spaced a predetermined distance in opposed relation, left and right flexible connection wall portions 6 respectively connecting left and right edges of the front rigid wall potion to left and right edges of the rear rigid wall portion, and has an anteroposterior thickness AT which is smaller than a lateral width LW thereof. The rigid wall portions 5 (front and rear wall portions) each have a vertically elongated rectangular shape as viewed from the front side, and are generally planar in cross section and vertical section. The cross section and the vertical section are not necessarily required to be completely planar, but may be slightly curved. The flexible connection wall portions 6 (left and right wall portions) each have an arcuate shape with an anteroposteriorly middle portion thereof projecting laterally outward, and each have a curvature radius which is smaller than the length of the minor axis of the body 2. Upper edges of the rigid wall portions 5 are each connected to the shoulder portion 3 via a flexible upper connection portion 7, and lower edges of the rigid wall portions 5 are each connected to a bottom portion 2a of the body 2 via a flexible lower connection portion 8. Thus, the peripheries of the rigid wall portions 5 are each surrounded only by the flexible portions 6, 7, 8. Further, the front and rear rigid wall portions 5 are integrally connected to the bottom portion 2a and the shoulder portion 3 only by the flexible portions 6, 7, 8, with the front wall portion rearwardly recessed from the upper and lower connection portions 7, 8, as see in FIG. 4.

The flexible upper connection portion 7 and the flexible lower connection portion 8 are located anteroposteriorly outward of the rigid wall portions 5. Therefore, when the bottle 1 is blow-molded from the plastic parison, portions of the parison corresponding to the connection portions 7, 8 are stretched at a higher stretch ratio, so that the connection portions 7, 8 are formed as having a relatively small thickness. As a result, the connection portions 7, 8 each have flexibility sufficient for easy deformation. On the other hand, the rigid wall portions 5 each have a greater thickness and, hence, are difficult to deform with high rigidity. The average thickness of the connection portions 7, 8 are preferably smaller than one half the average thickness of the rigid wall portions 5.

The lateral width of the body 2 of the squeeze bottle 1 is greater than 1.5 times the anteroposterior thickness of the body 2 (i.e., a distance between outer surfaces of the front and rear rigid wall portions 5). In the blow molding, portions of the parison corresponding to the left and right connection wall portions 6 are stretched at a higher stretch ratio, so that the average thickness of the left and right flexible connection wall portions 6 is smaller than the average thickness of the rigid wall portions 5. In the blow molding, portions of the parison corresponding to the rigid wall portions 5 may have a greater thickness than the portions of the parison corresponding to the flexible connection wall portions.

The thicknesses of the front and rear wall portions 5 and left and right wall portions 6 are selected so that: a) the front and rear wall portions can be pressed towards each other by squeezing forces applied by fingers of a user without being significantly warped; and b) the left and right wall portions are elastically deformable by the squeezing forces applied by the user's fingers to the front and rear walls to allow the front and rear walls to be moved towards each other.

When vertically middle portions of the front and rear rigid wall portions 5 of the outer layer bottle 1 having the aforesaid construction are pressed by two fingers to be displaced toward each other to positions spaced a distance which is one half the original distance between the middle portions, the left and right connection portions 6 and the upper and lower connection portions 7, 8 are deformable within an elastically deformable range so that the upper and lower edges of the rigid wall portions 5 follow the displacement of the middle portions.

In this embodiment, an introduction hole 17 for introducing outside air into a space between the bottle body 2 and a body 16b of the bag 16 is provided in a center portion of the front rigid wall portion 5 (front wall portion) of the outer layer bottle 1. The introduction hole 17 extends through the outer layer bottle 1 from the inner surface to the outer surface of the outer layer bottle, but the inner layer bag 16 has no introduction hole. Further, a round recess 18 having a greater diameter than the introduction hole 17 is provided in the center portion of the rigid wall portion 5. The recess 18 is indented inward of the bottle, and the diameter thereof is about 5 mm. The introduction hole 17 is provided in the recess 18. The introduction hole 17 can be closed by closing the recess 18 by a finger. The introduction hole 17 has no check valve and, hence, is always open. The introduction hole 17 has an opening area of about 1 mm$^2$ to about 2 mm$^2$.

Test holes 19 are provided in a vertically middle portion of the mouth portion 4 of the outer layer bottle 1 as communicating with the introduction hole 17 via the space between the outer layer bottle 1 and the inner layer bag 16. In this embodiment, two test holes 19 are provided at diametrically opposite positions. The test holes 19 also extend through the outer layer bottle 1 from the inner surface to the outer surface of the outer layer bottle, but the inner layer bag 16 has no test hole. The test holes 19 are closed from the inside by a mouth portion 16a of the inner layer bag 16, so that air between the outer layer 1 and the inner layer 16 is prevented from flowing out of the test holes 19 during use of the eyedropper 10. In order to assuredly close the test holes by the inner layer bag 16, the mouth portion 16a of the inner layer bag 16 is pressed against the test holes by an inside plug 21 to be described layer in this embodiment. Thus, the test holes 19 are closed by the inner layer bag 16 and the inside plug 21.

The body 16b of the inner layer bag 16 is of a film shape, and is easily deformable to be shrunk as the volume of the contents is reduced. On the other hand, the mouth portion 16a of the inner layer bag 16 has a greater thickness than the body 16b, and can recover its original cylindrical shape. The center of a bottom portion of the bag 16 is fixed to the center of the bottom portion of the outer layer bottle 1, so that the bottom portion of the bag 16 is prevented from being lifted.

The mouth plug 12 mainly includes an inside plug 21 fitted in the bottle mouth portion 4 and a nozzle cap 22 axially connected to the inside plug 21 and fitted around the bottle mouth portion 4.

The inside plug 21 is such that a first cylindrical portion 21a with its proximal end abutting against a distal end surface of the bottle mouth portion 4 and a second cylindrical portion 21b disposed in the first cylindrical portion 21a are integrally connected to each other via a flange 21c projecting radially outward from a distal edge of the second cylindrical portion 21b. A proximal end portion of the second cylindrical portion 21b extends much further than the proximal end of the first cylindrical portion 21a toward the proximal end of the inside plug (downward in FIG. 1), so that the second cylindrical portion 21b is fitted in the bottle mouth portion 4 in a gas-tight and liquid-tight manner. Particularly in this embodiment, the second cylindrical portion 21b extends further downward of the test holes 19 which are gas-tightly closed from the inside by the second cylindrical portion 21b.

A horizontal planar support wall portion 21d is provided in an axially middle portion of the second cylindrical portion 21b. The support wall portion 21d has four through-holes 23 (outlet passage) provided in a peripheral portion thereof around the center thereof as extending axially therethrough. A recess in which a connector sleeve 24a and a valve head 24b of a dispense valve 24 to be described later are fitted is provided above the support wall portion 21d.

The nozzle cap 22 is a generally cylindrical member, which includes a top plate provided with the nozzle portion 15 at its axially distal end. The first cylindrical portion 21a of the inside plug 21 is fitted in the nozzle cap 22. The nozzle cap 22 has a smaller diameter cylindrical portion provided in a distal outer peripheral portion thereof with a step. The protective cap 13 is threadingly fitted around the smaller diameter cylindrical portion.

A thin plate filter 25 is provided in a center portion of a lower surface of the top plate of the nozzle cap 22. Examples of the filter 25 include a membrane filter, a sintered filter, a hydrophilic porous planar film and a hydrophobic porous planar film, which are capable of preventing passage of pathogenic bacteria from a downstream side to an upstream side of the outlet passage (from the outside to the inside of the bottle). The filter 25 is disposed downstream of the dispense valve 24. In the illustrated example, the filter is disposed adjacent the nozzle portion 15, and held above the inside plug 21 by a holder 26 fitted in the nozzle cap 22. The holder 26 has a through-hole 26a through which the content liquid flows into the filter 25. Therefore, the outlet passage of the mouth plug 12 communicating between the inside of the bag 16 and the outside of the bottle is constituted by the through-holes 23, a cavity, the through-hole 26a and an inside passage of the nozzle portion 15.

The dispense valve 24 is constituted by a valve flange 24c, the valve head 24b and the connector sleeve 24a which are integrally formed of an elastic material such as a silicone rubber.

The valve flange 24c is a generally ring member, which has a triangular cross section having a thickness gradually increasing toward its outer periphery. The valve flange 24c is held vertically between the inside plug 21 and the nozzle cap 22 in a gas-tight and liquid-tight manner to air-tightly and liquid-tightly seal the inner periphery of the outlet passage.

The valve head 24b has a semispherical shape which is round as seen in plan and concavely curved inwardly of the bottle, and has an orifice of a cross shape incised in a center portion thereof. The orifice is opened to permit the fluid (content liquid) to flow from the inside of the inner layer bag 16 when a predetermined dispense pressure is applied to an inner surface of the head 24b, and closed to block the flow of the fluid when the predetermined dispense pressure is removed. A lower surface of the valve head 24b has a generally flat center portion, and the orifice 24d is provided in the flat surface portion. The flat surface portion of the valve head 24b usually abuts against an upper surface of the support wall portion 21d.

The connector sleeve 24a has a generally cylindrical shape with its one axial end integrally connected to an inner peripheral edge of the valve flange 24c and with its other axial end integrally connected to an outer peripheral edge of the valve head 24b. The connector sleeve 24a has a relatively thin flexible structure so as to be easily deformable. Thus, when a predetermined pressure smaller than the aforesaid predetermined dispense pressure is applied to the inner surface of the valve head 24b, the valve head 24b is displaced downstream (toward the distal end) with the orifice 24d kept closed. As a result, the connector sleeve 24a is elastically deformed to be lifted. When the predetermined smaller pressure is removed, the connector sleeve 24a recovers its original shape, whereby the valve head 24b is displaced upstream (toward the proximal end) with the orifice 24d kept closed. As a result, the fluid remaining in the nozzle inside passage is sucked back to the upstream side of the filter. A fluid suction force may be provided by the recovery force of the connector sleeve 24a or by a negative pressure applied to the inner surface of the head 24b.

The structure of the connector sleeve 24a is not limited to that shown in the figure, but may have an elastically deformable bellow structure which is axially shrinkable.

In the eyedropper 10, the valve head 24b is deformed toward the distal end with the orifice 24d of the dispense valve 24 kept closed when the inside pressure is increased within a range smaller than the predetermined dispense pressure due to a temperature change or during carrying of the eyedropper. The inside pressure is reduced according to the amount of the displacement of the valve head 24b, so that the pressure increase is alleviated. For dispensing the content liquid from the nozzle portion 15, the user holds the bottle 11 upside down and presses the body 2 of the outer layer bottle 1 radially inward from opposite sides of the minor axis of the bottle with the introduction hole 17 closed by the finger as shown in FIG. 2. Thus, the outer layer bottle 1 is squeezed to be deformed to pressurize the air in the space between the outer layer 1 and the inner layer 16, whereby the inner layer bag 16 is compressed. When an inside pressure not smaller than the predetermined dispense pressure is thus applied to the inner surface of the head 24b, the orifice 24d of the dispense valve 24 is opened to drop the content liquid from the inner layer bag 16 through the nozzle portion 15. When the user stops pressing the bottle 11 and releases the finger from the introduction hole 17, outside air is introduced into the space between the outer layer 1 and the inner layer 16 from the introduction hole 17. At this time, the valve head 24b first recovers its original shape to close the orifice 24d, and then the connector sleeve 24a recovers its original shape. When the sleeve 24a recovers its original shape, the content liquid remaining in the nozzle inside passage (i.e., a distal opening of the outlet passage) is sucked back into the cavity upstream of the filter 25. Then, the content liquid is retained in the cavity which is isolated from the outside air.

When the pressing of the delaminatable bottle 11 is stopped, the outer layer bottle 1 recovers its original shape, but the inner layer bag 16 does not recover its original shape without the back-flow of the content liquid into the inner layer bag 16 and without the introduction of the outside air because the orifice 24d is closed. Therefore, the inner layer bag is shrunk as the volume of the content liquid is reduced. On the other hand, when the outer layer bottle 1 recovers its original shape, air is introduced into the space between the inner layer bag 16 and the outer layer bottle 1 through the introduction hole 17. Even if a negative pressure occurs inside the inner layer 16 at this time to apply a force to the valve head 24b of the dispense valve 24 to deform the valve head inward of the bottle, the orifice is opened by the inward deformation of the head 24b and, therefore, the outside air is prevented from flowing into the inner layer bag 16. This is because the head 24b is supported in abutment against the support wall portion 21d and, hence, has a flexible structure as described above.

Next, a production method and a production apparatus for the aforementioned delaminatable laminated bottle will be explained by way of embodiments thereof with reference to FIGS. 7 to 11.

Figure 10:
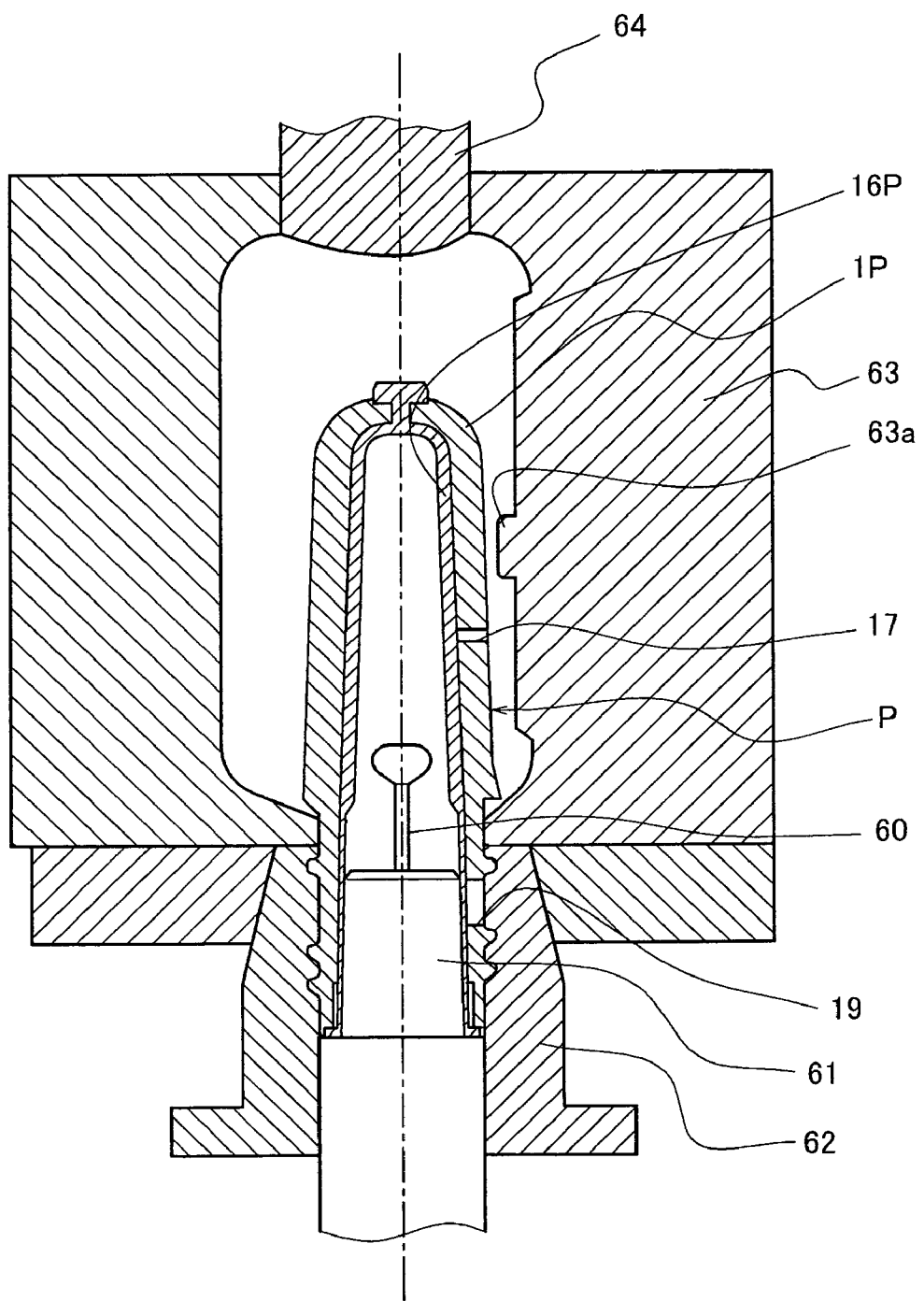
FIG. 10 is a schematic vertical sectional view illustrating a blow-molding mold employed in a blow molding step of the production method as corresponding to the sectional view taken along the line C-C in FIG. 9.
Figure 11:
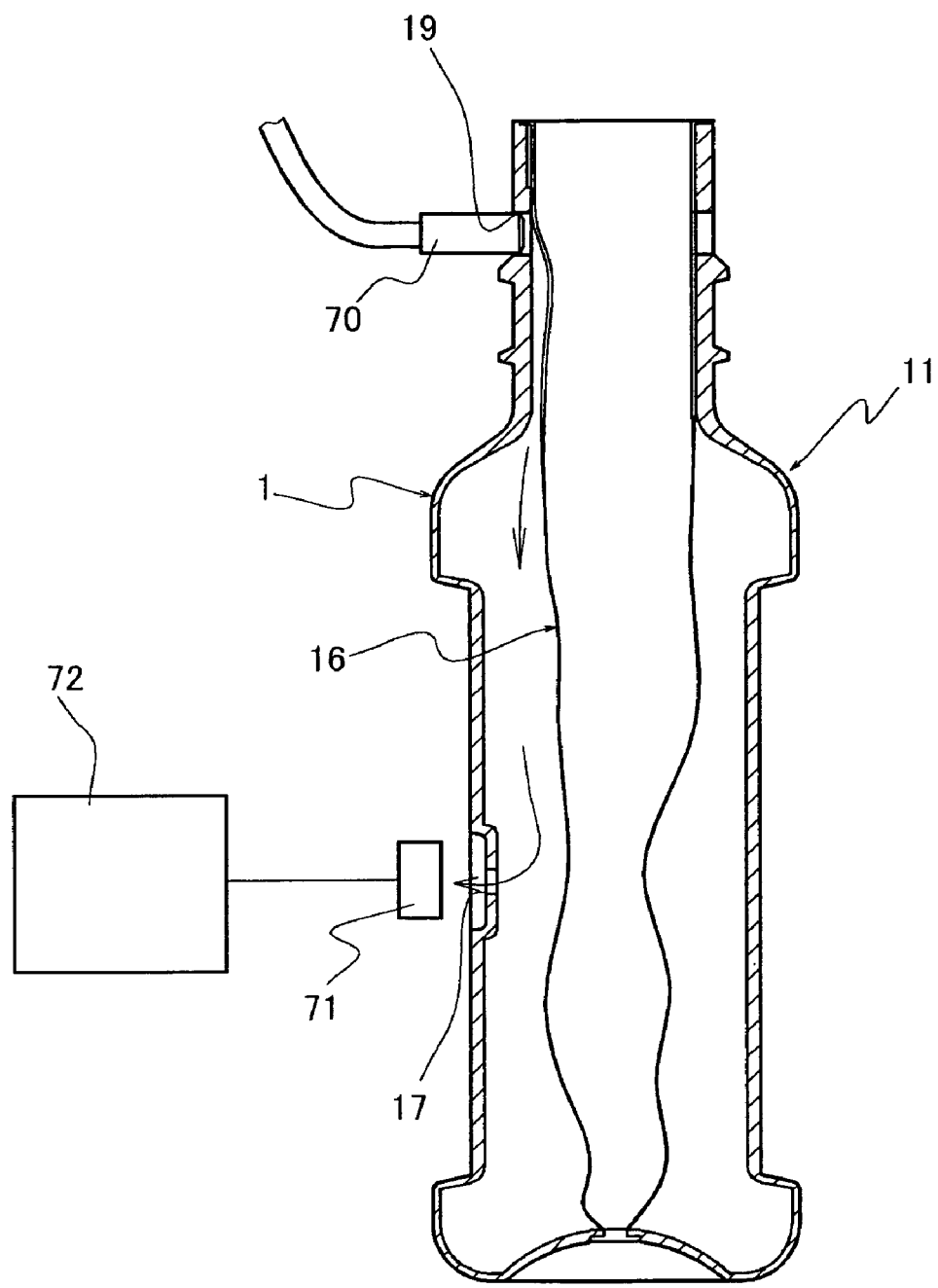
FIG. 11 is a schematic diagram illustrating a defective product checking step of the production method.

The production method according to this embodiment includes the steps of injection-molding an outer layer preform 1P (see FIG. 7), injection-molding an inner layer preform 16P on the entire inner surface of the outer layer preform 1P (see FIG. 8), blow-molding the delaminatable laminated bottle 11 in a biaxially stretchable manner from a laminate parison P (see FIG. 9) including the outer layer preform 1P and the inner layer preform 16P (see FIG. 10), and performing a defective checking operation (see FIG. 11).

Figure 7:
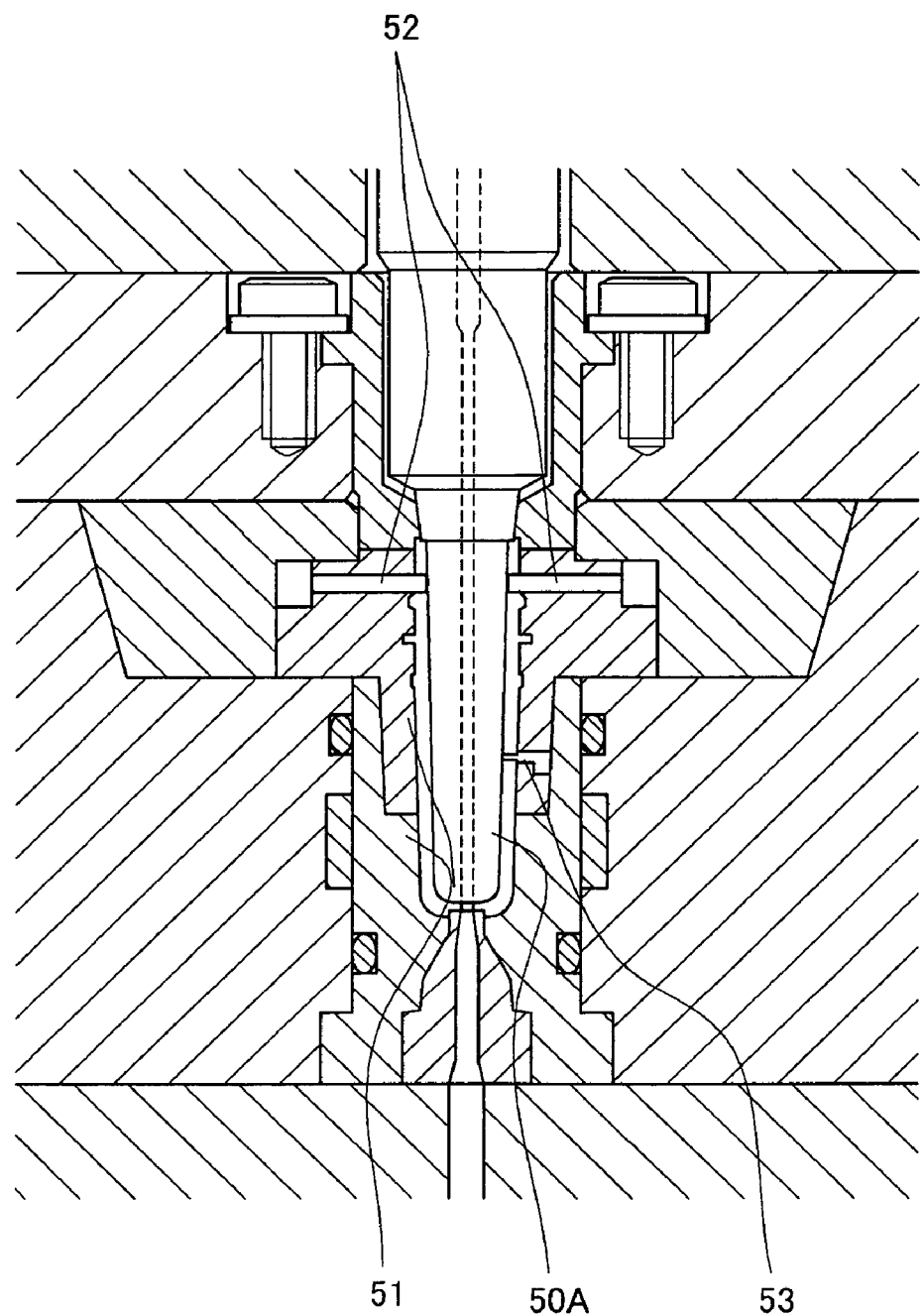
FIG. 7 is a vertical sectional view of a mold for illustrating an outer layer preform injection molding step of a delaminatable laminated bottle production method according to another embodiment of the present invention.
Figure 8:
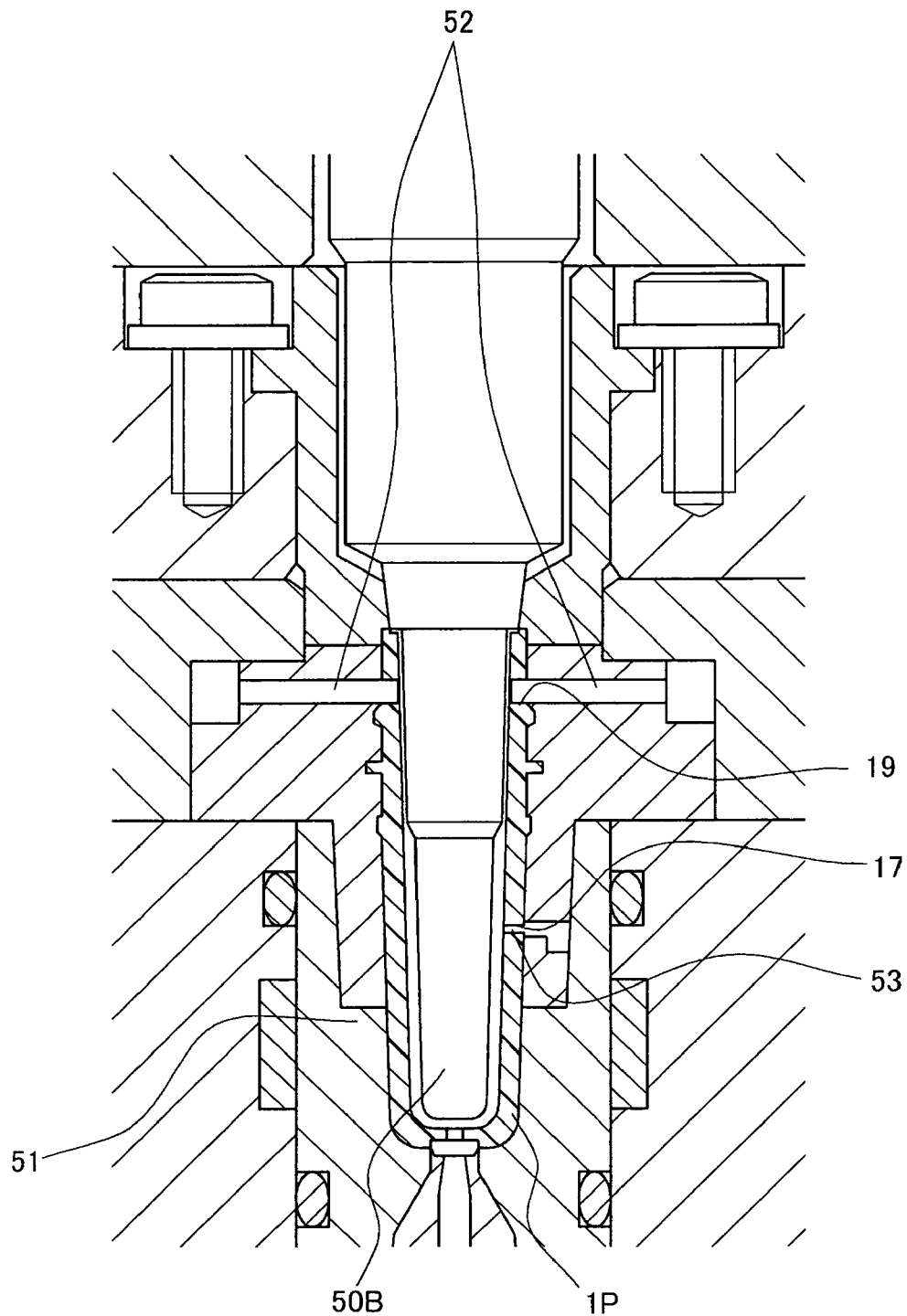
FIG. 8 is a vertical sectional view of a mold for illustrating an inner layer preform injection molding step of the production method.

The outer layer preform 1P and the inner layer preform 16P are molded by means of an injection station shown in FIGS. 7 and 8. In this embodiment, the outer layer preform and then the inner layer preform are molded in the same position in the same station by changing an injection core. However, a mold for the injection molding of the outer layer preform and a mold for the injection molding of the inner layer preform may be separately provided.

FIG. 7 illustrates the step of molding the outer layer preform 1P. In this figure, the injection-molding mold includes injection cores 50A, 50B arid a cavity mold 51. After the injection core and the cavity mold are vertically combined with each other and clamped, a melted resin is injected into the cavity through a hot runner and a hot runner nozzle to mold the outer layer preform 1P.

Pins 52, 53 for forming the introduction hole 17 and the test holes 19 are provided in positions in the cavity mold 51. These pins 52, 53 project radially inward from the cavity mold 51. Distal ends of the pins abut against a side surface of the injection core 50A during the injection of the melted resin (before the start of the injection or after the injection before the resin is cured). When the outer layer preform 1P is molded, the introduction hole 17 and the test holes 19 are formed as extending through the outer layer preform by these pins 52, 53. The pins 52, 53 are adapted to be withdrawn radially outward from the introduction hole 17 and the test holes 19 by opening the cavity mold.

FIG. 8 illustrates the step of molding the inner layer preform 16P. A state illustrated in FIG. 8 is such that another injection core 50B for the inner layer is inserted after the outer layer preform 1P is molded and the injection core 50A for the outer layer is withdrawn. The pins 52, 53 are kept in the state shown in FIG. 7. That is, the pins 52, 53 are inserted from the outer periphery with the distal ends thereof being flush with the inner surface of the outer layer preform 1P. The inner layer injection core 50B has a diameter which is smaller than the outer layer injection core 50A by the thickness of the inner layer preform 16P. The injection core 50B may have a resin flow path and a gate for injecting a melted resin for the inner layer preform 16P into a cavity.

Figure 9:
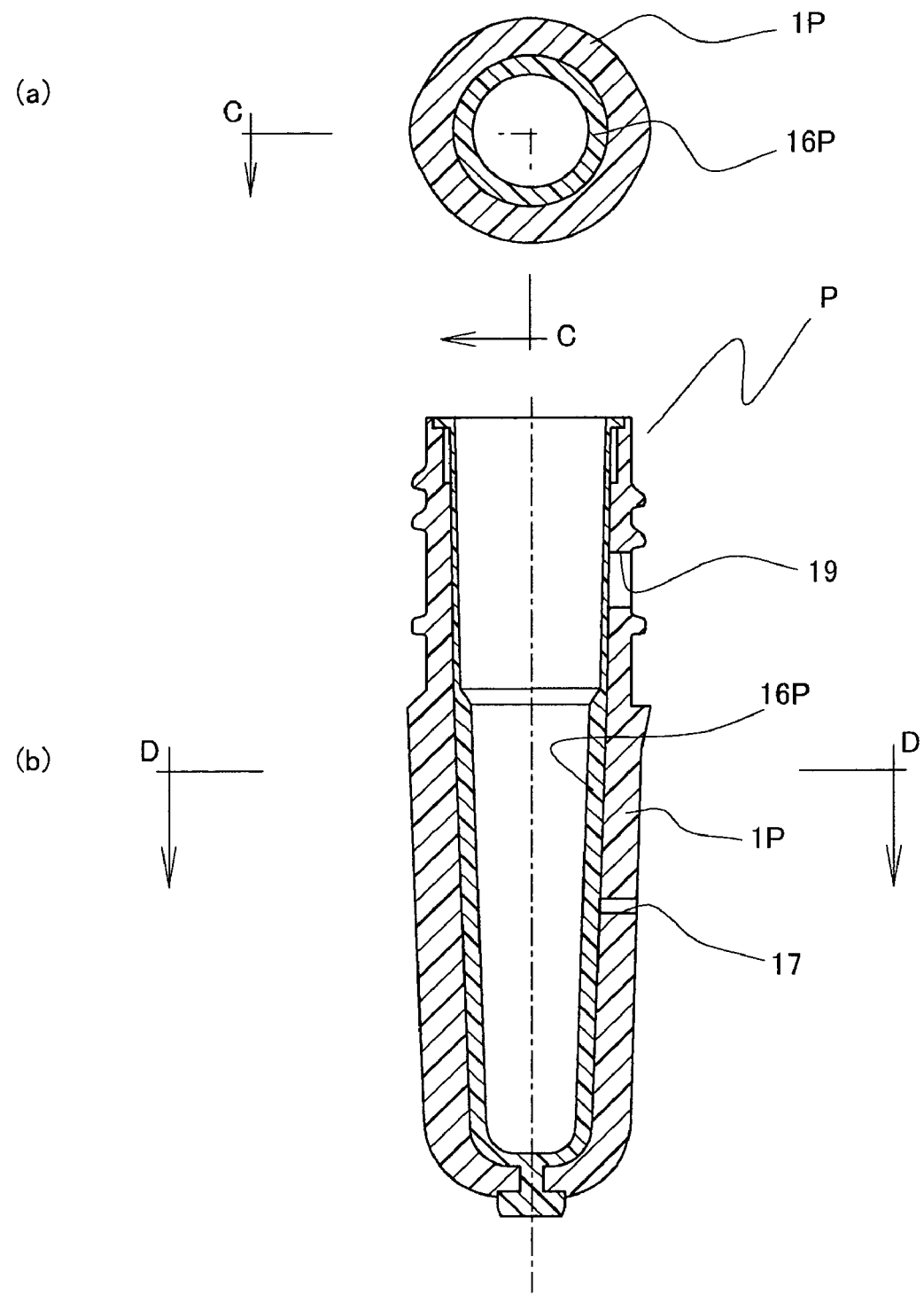
FIGS. 9(a) and 9(b) illustrate a laminate parison as an intermediate product obtained by the production method, particularly.

After the inner layer preform 16P is molded, the injection-molding mold is opened to take out the laminate parison P, which is in turn transported to a blow station. As shown in FIG. 9, portions of a body of the laminate parison P corresponding to the rigid wall portions 5 of the bottle 1 have a greater thickness than portions of the laminate parison P corresponding to the connection wall portions 6, 7. The laminate parison P has a positioning reference portion Ps (see FIGS. 4 and 5) provided in a predetermined circumferential position on an outer periphery of a mouth portion of the laminate parison P for positioning the laminate parison P circumferentially with respect to a mold for the blow molding. The introduction hole 17 of the outer layer preform 1P has a diameter of about 0.7 mm, and a portion of the inner layer preform 16P adjacent to the introduction hole has a thickness of about 0.8 mm.

In the blow station shown in FIG. 10, the delaminatable laminated bottle 11 is blow-molded from the parison P with the use of the blow-molding mold which includes a blow core 61 fitted with a draw rod 60, a lip mold 62 for holding the parison P, a blow cavity mold 63 and a bottom mold 64. A shape imparting surface of the blow cavity mold 63 includes a shape imparting surface portion 63a for forming the recess 18 in the center portion of the rigid wall portion 5 of the outer layer bottle 1 around the introduction hole 17.

When the parison P is inserted in the blow-molding mold, the parison P is first rotated so that the reference portion Ps of the parison P is located in a predetermined angular position with respect to the blow-molding mold. The positional adjustment may be performed by pressing the reference portion Ps by mechanical contact or by rotating the parison P while checking the position of the reference portion Ps by an optical sensor, a CCD camera or the like. When the blow-molding mold is clamped, the parison P is fixed in an accurate position with the reference portion Ps being held by the mold. The temperature of the parison P is preliminarily adjusted before the parison P is inserted into the blow-molding mold.

After the clamping of the blow-molding mold, the parison P is first vertically drawn by moving down the draw rod 60 to press the bottom of the bottomed cylindrical parison P downward. Then, pressurized air is introduced into the parison P from the blow core 61 to laterally draw the parison P, whereby the body of the parison P is pressed against the shape imparting surface of the cavity mold 63. Thus, the bottle body is shaped. At this time, the portion (bottle mouth portion) of the parison formed with the test holes 19 is held by the lip mold 62 and, therefore, is not drawn. However, a portion of the parison downward of the test holes 19 is drawn. The portion of the parison formed with the introduction hole 17 is vertically and laterally drawn. However, the positional and configurational variations of the introduction hole 17 formed in the bottle after the blow molding are less conspicuous, because the blow molding is performed with the introduction hole 17 being located in the shape imparting surface portion 63a. When the parison is laterally drawn, the introduction hole 17 is prevented from being buried in the inner layer preform 16P because the thickness of the portion of the inner layer preform 16P around the introduction hole 17 is greater than the diameter of the introduction hole 17. The thickness is not greater than about twice the diameter of the introduction hole 17.

After the blow molding, the delaminatable laminated bottle 11 thus molded is taken out. The inner layer bag 16 is preferably once delaminated from the outer layer bottle 1 by sucking air out of the inner layer bag 16 by vacuum.

In the defective checking step shown in FIG. 11, an injection nozzle 70 connected to a pump is inserted in the test hole 19, and air is injected into the space between the outer layer bottle 1 and the inner layer bag 16 from the test hole 19 through the injection nozzle 70. An air communication detection sensor 71 such as a pressure sensor is provided in the vicinity of the introduction hole 17. Whether or not the air flows out of the introduction hole 17 is checked during the injection of the air from the test hole 19. By inputting a detection signal from the sensor to a control device 72 such as a computer, an air communication test is performed for checking the air communication between the test hole 19 and the introduction hole 17, whereby defectiveness of the introduction hole 17 is checked. A production line is designed so that defective bottles are automatically screened out based on the result of the check.

The present invention is not limited to the arrangements described in the embodiments, but may be arbitrarily modified within a technical scope defined by the appended claims.

According to the present invention, check means for checking defectiveness of the outside air introduction hole is provided for the small delaminatable laminated bottle, particularly for an eyedropper having a volume of about 10 ml. Even without the provision of a check valve in the introduction hole, the introduction hole can be easily closed when the bottle body is squeezed. The air in the space between the inner layer and the outer layer is assuredly compressed to dispense a relatively great amount of content liquid at a time by squeezing the bottle body.

What is claimed is:

1. A delaminatable laminated bottle comprising:
   an outer layer bottle having a squeeze-deformable bottomed tubular body, a shoulder portion and a mouth portion connected to an upper edge of the body via the shoulder portion; and
   an inner layer bag provided on an inner surface of the outer layer bottle and delaminatable from the outer layer bottle;
   wherein the outer layer bottle has an introduction hole for introducing outside air into a space between the outer layer bottle and the inner layer bag;
   wherein the body of the outer layer bottle has a flat tubular peripheral wall which includes a pair of generally flat front and rear wall portions spaced a predetermined distance in opposed relation and left and right wall portions respectively connecting left and right edges of the front wall portion to left and right edges of the rear wall portion, and has an anteroposterior thickness which is smaller than a lateral width thereof,
   wherein the left and right wall portions each have an arcuate shape with an anteroposteriorly middle portion thereof bulged laterally outward,
   wherein the body further has an upper connection portion which connects upper edges of the front and rear wall portions to the shoulder portion, and a lower connection portion which connects lower edges of the front and rear wall portions to a bottom portion thereof,
   wherein the introduction hole is provided in one of the front wall portion and the rear wall portion,
   wherein the introduction hole is adapted to be closed by a finger when the body is squeezed to be deformed by pressing the front and rear wall portions by the finger,
   the front and rear wall portions having a thickness,
   the left and right wall portions having a thickness,
   the thicknesses of the front and rear wall portions and left and right wall portions selected so that: a) the front and rear wall portions can be pressed towards each other by squeezing forces applied by fingers of a user without being significantly warped; and b) the left and right wall portions are elastically deformable by the squeezing forces applied by the user's fingers to the front and rear walls to allow the front and rear walls to be moved towards each other,
   wherein the connection portions have a thickness and an average thickness of at least one of the connection portions is less than one half an average thickness of the front and rear wall portions.

2. The delaminatable laminated bottle according to claim 1 wherein the average thickness of both of the connection portions is less than one half the average thickness of the front and rear wall portions.

3. A delaminatable laminated bottle comprising:
   an outer layer bottle having a squeeze-deformable bottomed tubular body, a shoulder portion and a mouth portion connected to an upper edge of the body via the shoulder portion; and
   an inner layer bag provided on an inner surface of the outer layer bottle and delaminatable from the outer layer bottle;
   wherein the outer layer bottle has an introduction hole for introducing outside air into a space between the outer layer bottle and the inner layer bag;
   wherein the body of the outer layer bottle has a flat tubular peripheral wall which includes a pair of front and rear wall portions that are either planar or slightly curved and spaced a predetermined distance in opposed relation and left and right wall portions respectively connecting left and right edges of the front wall portion to left and right edges of the rear wall portion, and has an anteroposterior thickness which is smaller than a lateral width thereof,
   wherein the left and right wall portions each have an arcuate shape with an anteroposteriorly middle portion thereof bulged laterally outward,
   wherein the body further has an upper connection portion which connects upper edges of the front and rear wall portions to the shoulder portion, and a lower connection portion which connects lower edges of the front and rear wall portions to a bottom portion thereof,
   wherein the introduction hole is provided in one of the front wall portion and the rear wall portion,
   wherein the introduction hole is adapted to be closed by a finger when the body is squeezed to be deformed by pressing the front and rear wall portions by the finger,
   the front and rear wall portions having a thickness,
   the left and right wall portions having a thickness,
   the thicknesses of the front and rear wall portions and left and right wall portions selected so that: a) the front and rear wall portions can be pressed towards each other by squeezing forces applied by fingers of a user without being significantly warped; and b) the left and right wall portions are elastically deformable by the squeezing forces applied by the user's fingers to the front and rear walls to allow the front and rear walls to be moved towards each other, wherein an average thickness of the left and right wall portions is less than an average thickness of the front and rear wall portions, wherein the connection portions have a thickness and an average thickness of the connection portions is less than one half the average thickness of the front and rear wall portions.

4. The delaminatable laminated bottle according to claim 3 wherein the average thickness of both of the connection portions is less than one half the average thickness of the front and rear wall portions.

* * * * *